United States Patent
Priest et al.

(10) Patent No.: US 11,557,389 B2
(45) Date of Patent: Jan. 17, 2023

(54) METHODS AND COMPUTER PROGRAM PRODUCT FOR APPLICATION-BASED TELEMEDICINE FOR PERFORMING A CLEANING OPERATION ON THE EAR CANAL OF A PATIENT

(71) Applicant: Nupur Technologies, LLC, Buffalo, NY (US)

(72) Inventors: Joseph L. Priest, Lewiston, NY (US); Rohan Bansal, Buffalo, NY (US)

(73) Assignee: Nupur Technologies, LLC, Buffalo, NY (US)

( * ) Notice: Subject to any disclaimer, the term of this patent is extended or adjusted under 35 U.S.C. 154(b) by 45 days.

(21) Appl. No.: 16/904,062

(22) Filed: Jun. 17, 2020

(65) Prior Publication Data
US 2020/0402637 A1 Dec. 24, 2020

Related U.S. Application Data

(60) Provisional application No. 62/864,179, filed on Jun. 20, 2019.

(51) Int. Cl.
*G16H 20/30* (2018.01)
*G16H 40/20* (2018.01)
*G16H 40/67* (2018.01)

(52) U.S. Cl.
CPC ........... *G16H 20/30* (2018.01); *G16H 40/20* (2018.01); *G16H 40/67* (2018.01)

(58) Field of Classification Search
CPC ........ G16H 20/30; G16H 40/20; G16H 40/67
See application file for complete search history.

(56) References Cited

U.S. PATENT DOCUMENTS

| | | | |
|---|---|---|---|
| 4,998,672 A | 3/1991 | Bordaz et al. |
| 5,170,779 A | 12/1992 | Ginsberg |
| 5,309,899 A | 5/1994 | Ginsberg |
| 5,527,275 A | 6/1996 | Ginsberg |
| 5,662,605 A | 9/1997 | Hurwitz |
| 5,869,954 A | 2/1999 | Kurz |
| D462,437 S | 9/2002 | Epstein et al. |
| 6,485,451 B1 | 11/2002 | Roberts et al. |
| 8,328,830 B1 | 12/2012 | Pandit |
| D749,716 S | 2/2016 | Holmgren et al. |
| 9,993,591 B2 | 6/2018 | Bansal et al. |
| 2005/0010084 A1 | 1/2005 | Tsai |
| 2005/0279197 A1 | 12/2005 | Wottreng, Jr. et al. |

(Continued)

OTHER PUBLICATIONS

"Nupur Technologies: Earigator" <https://web.archive.org/web/20150426194438/http://nupurtech.com:80/index.htm> Apr. 26, 2015.

*Primary Examiner* — Sheetal R Paulson
(74) *Attorney, Agent, or Firm* — Bond, Schoeneck & King, PLLC

(57) ABSTRACT

Systems, methods, and a computer program product are provided which establish application-based telemedicine methods and protocols for providing authorization to an unlicensed or licensed user to perform a cleaning operation on a patient's ear canal. Specifically, once the user determines that a cleaning operation is necessary, an application is provided which allows the user to consolidate relevant information regarding the patient, send the relevant patient information along with a permission request to a licensed medical professional, receive an approved permission request, and perform a cleaning operation on the patient.

18 Claims, 11 Drawing Sheets

(56) References Cited

U.S. PATENT DOCUMENTS

| | | |
|---|---|---|
| 2006/0087283 A1 | 4/2006 | Phillips et al. |
| 2010/0137814 A1 | 6/2010 | Chew |
| 2012/0059224 A1 | 3/2012 | Wellen et al. |
| 2013/0123701 A1 | 5/2013 | Hernandez Chafes |
| 2014/0166324 A1 | 6/2014 | Puzio et al. |
| 2016/0279321 A1 | 9/2016 | Bansal et al. |

METHODS AND COMPUTER PROGRAM PRODUCT FOR APPLICATION-BASED TELEMEDICINE FOR PERFORMING A CLEANING OPERATION ON THE EAR CANAL OF A PATIENT

CROSS-REFERENCE TO RELATED APPLICATIONS

This application claims the benefit of U.S. Provisional Patent Application No. 62/864,179 filed on Jun. 20, 2019, which application is hereby incorporated by reference in its entirety.

BACKGROUND

Aspects and implementations of the present disclosure are generally directed to methods and computer program products for application-based telemedicine, specifically, to web or network-based telemedicine related to performing a cleaning operation of a patient's ear canal.

When a patient begins experiencing some type of hearing loss, the patient may seek out a hearing aid dispenser (HAD) and schedule an appointment to have their hearing tested. The HAD is typically staffed by a hearing instrument specialist (HIS), typically licensed by the state, or a doctor of audiology (AuD). Both the HIS and the AuD are permitted to test for hearing loss and dispense hearing aids. The primary method to determine hearing loss involves administration of a hearing test using an audiometer and a sound booth or quiet room.

Prior to administering the hearing test, the HIS or AuD examines the patient's ear canal using an otoscope to look directly into the patent's ear to determine if there are any anatomical anomalies or anything that appears to obstruct the patient's ear canal. Often, this examination results in an observation of excessive or impacted cerumen (ear wax) within the ear canal. If an excessive build-up of cerumen is detected, it is typically understood that a hearing test cannot be conducted properly, i.e., the results may not be accurate. To conduct a proper hearing test, the excess cerumen needs to be removed.

Typically, removal of the build-up can include manual removal (e.g., using a curette), suction, or irrigation. Regardless of the method employed, various state and federal regulations recommend referring a patient experiencing excessive cerumen build-up to a licensed medical professional, e.g., an Ear, Nose & Throat (ENT) Doctor, for removal. Referral of patients to medical professionals creates a large inconvenience for the patient as well as the HIS/AuD. What could have been addressed in one visit to the HAD, can easily turn into three or more visits (e.g., the initial visit to the HAD, the second visit to the ENT, and the return visit to the HAD for the hearing test to be performed). Furthermore, in the event that the ear canal was not successfully cleaned the hearing test may need to be postponed further for an additional visit to a licensed medical professional for a subsequent cleaning.

The present disclosure relates to systems, methods, and a computer program product directed to application-based telemedicine methods and protocols for providing authorization to an unlicensed or licensed user to perform a cleaning operation on a patient's ear canal. Specifically, once the user determines that a cleaning operation is necessary, an application is provided which allows the user to consolidate relevant information regarding the patient, send the relevant patient information along with a permission request to a licensed medical professional, receive an approved permission request, and perform a cleaning operation on the patient.

In one example, a method for providing authorization to perform a cleaning operation on a patient is provided, the method including: determining whether an ear canal of the patient requires a cleaning operation; sending, via an application, a permission request to a licensed medical professional, the permission request corresponding with a request for permission to perform a cleaning operation of the patient's ear canal; receiving, via the application, a granted permission request from the licensed medical professional; and performing a cleaning operation of the ear canal of the patient.

In one aspect, performing the cleaning operation of the patient's ear canal includes manually cleaning the patient's ear canal, cleaning the patient's ear canal using suction, or cleaning the patient's ear canal using an irrigation system.

In one aspect, manually cleaning the patient's ear canal comprises using a curette, forceps, or tweezers.

In one aspect, the irrigation system includes a portable applicator arranged to engage with and perform a cleaning operation on the ear canal of the patient, a liquid reservoir arranged to contain a fluid, the liquid reservoir comprising a heater for heating the fluid, and a control unit operatively arranged to control the heater of the liquid reservoir and operatively arranged to control a pump arranged between the liquid reservoir and the portable applicator such that the control unit can dynamically vary a flow rate of the fluid from the portable applicator.

In one aspect, determining whether the patient is eligible for receiving a cleaning operation, where determining eligibility includes whether the patient has experienced trauma. pain in their ear canal, or has previously had surgery related to their ear.

In one aspect, the method further includes obtaining an image from at least one camera, the image including medical information related to the patient, and sending, via the application, the image to the licensed medical professional.

In one aspect, the method further includes receiving, by the licensed medical professional, the permission request and determining, by the licensed medical professional, whether to grant or deny the permission request to perform the cleaning operation of the ear canal of the patient based at least in part on medical information related to the patient.

In one aspect, the licensed medical professional is selected from a plurality of licensed medical professionals in communication with the application.

In one aspect, the selection of the licensed medical professional from the plurality of licensed medical professionals is based on a status indicator provided by the application, or by an algorithm used by the application.

In one aspect, the application is configured to obtain statistical data relating a total number granted permission requests, a total number of denied permission requests, or an average time duration for granting or denying the permission requests.

In one example, a computer program product for obtaining authorization to perform a cleaning operation of a patient's ear canal is provided, the computer program product including a set of non-transitory computer-readable instructions stored on a memory that when executed on a processor are configured to: send a permission request to a licensed medical professional, the permission request corresponding with a request for permission to perform the cleaning operation of the patient's ear canal; and receive a granted permission request from the licensed medical professional; wherein the granted permission request prompts an individual to perform the cleaning operation of the patient's ear canal.

In one aspect, the cleaning operation of the patient's ear canal includes manually cleaning the patient's ear canal, cleaning the patient's ear canal using suction, or cleaning the patient's ear canal using an irrigation system.

In one aspect, manually cleaning the patient's ear canal comprises using a curette, forceps, or tweezers.

In one aspect, the irrigation system includes a portable applicator arranged to engage with and perform a cleaning operation on the ear canal of the patient; a liquid reservoir arranged to contain a fluid, the liquid reservoir comprising a heater for heating the fluid; and a control unit operatively arranged to control the heater of the liquid reservoir and operatively arranged to control a pump arranged between the liquid reservoir and the portable applicator such that the control unit can dynamically vary a flow rate of the fluid from the portable applicator.

In one aspect, the processor is further configured to obtain an image from at least one camera, the image including medical information related to the patient and send the image to the licensed medical professional.

In one aspect, the processor is further configured to: send and receive patient medical data related to determining whether the patient is eligible for receiving the cleaning operation, including whether the patient has experienced trauma, pain in their ear canal, or has previously had surgery related to their ear.

In one aspect, the processor is further configured to establish a connection with a plurality of licensed medical professionals.

In one aspect, the processor is further configured to: receive a user input selecting a licensed medical professional from the plurality of licensed medical professionals.

In one aspect, the selection of the licensed medical professional is selected based on a status indicator, or based on an algorithm.

In one aspect, the processor is further configured to obtain statistical data relating a total number granted permission requests, a total number of denied permission requests, or an average time duration for granting or denying the permission requests.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure relates to systems, methods, and a computer program product directed to application-based telemedicine methods and protocols for providing authorization to an unlicensed or licensed user to perform a cleaning operation on a patient's ear canal. Specifically, once the user determines that a cleaning operation is necessary, an application is provided which allows the user to consolidate relevant information regarding the patient, send the relevant patient information along with a permission request to a licensed medical professional, receive an approved permission request, and perform a cleaning operation on the patient.

Figure 1:
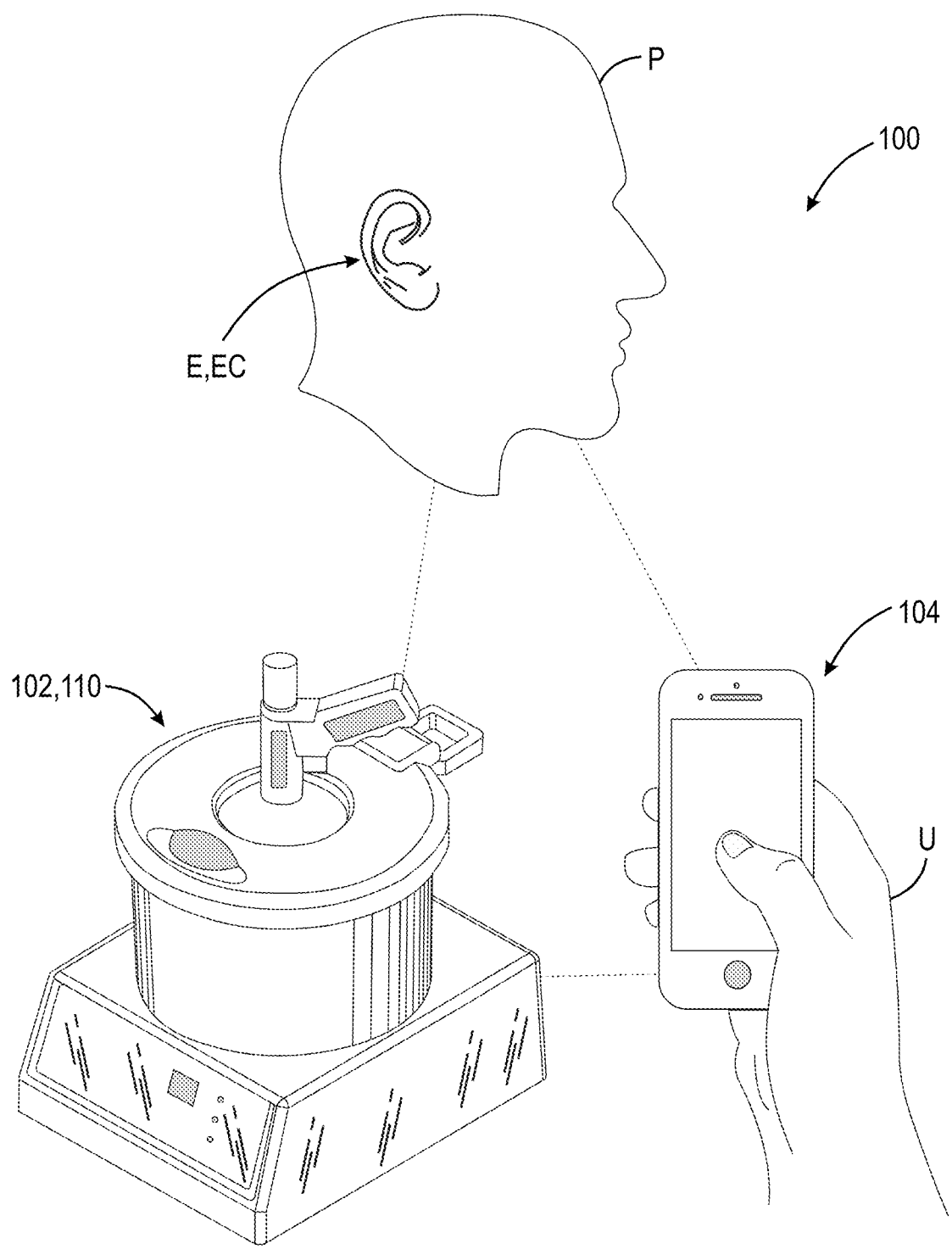
FIG. 1 is a schematic perspective view of a system according to the present disclosure.

The following description should be read in view of FIGS. 1-10. FIG. 1 is a schematic illustration of system 100 according to the present disclosure. System 100 is intended to be utilized by a user U, e.g., a licensed or unlicensed professional such as a HIS, discussed above. System 100 includes cleaning means 102 and a peripheral device 104. As will be discussed below in detail, the various cleaning operations discussed herein are performed on or in the ear canal EC of the ear E of patient P. Cleaning means 102 can be any means of performing a cleaning operation on patient P's ear canal EC. For example, as illustrated in FIGS. 2A-2C, cleaning means 102 can include manually cleaning the patient's ear canal EC using curette 106, cleaning the patient's ear canal EC using a suction system, e.g., suction system 108, and/or cleaning the patient's ear canal EC using an irrigation system, e.g., irrigation system 110. Additionally, although this disclosure primarily refers to and describes system 100 using irrigation system 110, it should be appreciated that manual cleaning operations using curette 106 and cleaning operations using suction system 108 are contemplated herein. Furthermore, in addition to or in the alternative to, the use of curette 106, manual cleaning means 102 can include using forceps and/or tweezers. Peripheral device 104 is intended to be a mobile phone, e.g., a smart phone. However, it should be appreciated that peripheral device 104 can be selected from a laptop, a mobile personal computer, a desktop personal computer, or any device capable of receiving a user input (e.g., user input 138 discussed below) and executing and displaying application 152 (also discussed below).

Figure 2A:
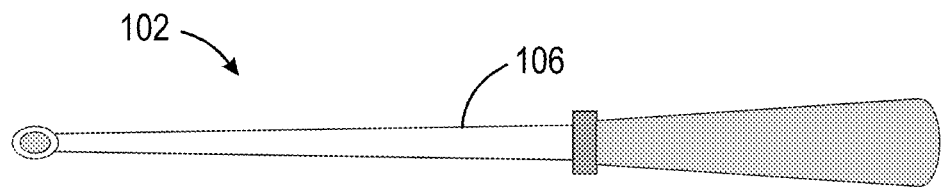
FIG. 2A is a schematic illustration of a cleaning means according to the present disclosure.
Figure 2B:
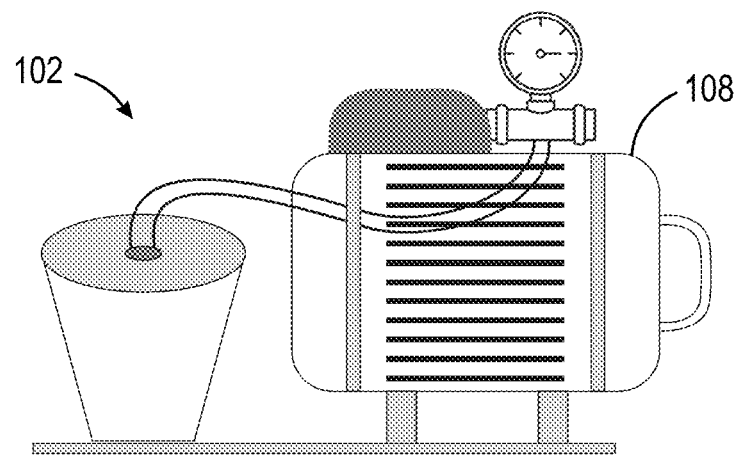
FIG. 2B is a schematic illustration of a cleaning means according to the present disclosure.
Figure 2C:
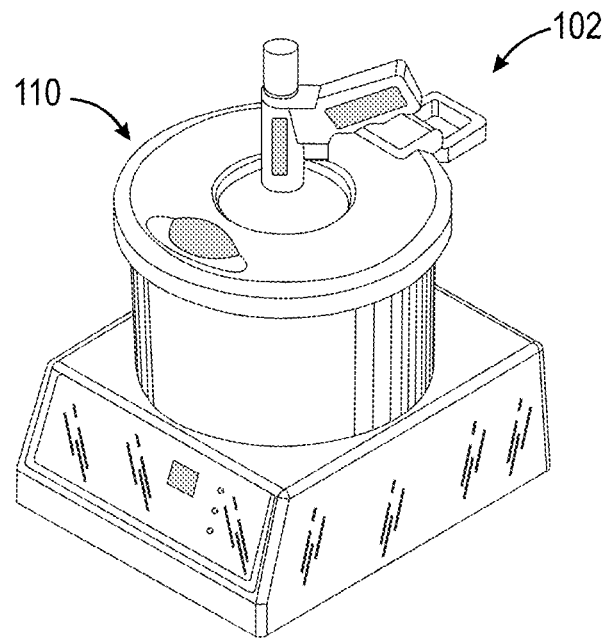
FIG. 2C is a schematic illustration of a cleaning means according to the present disclosure.
Figure 3:
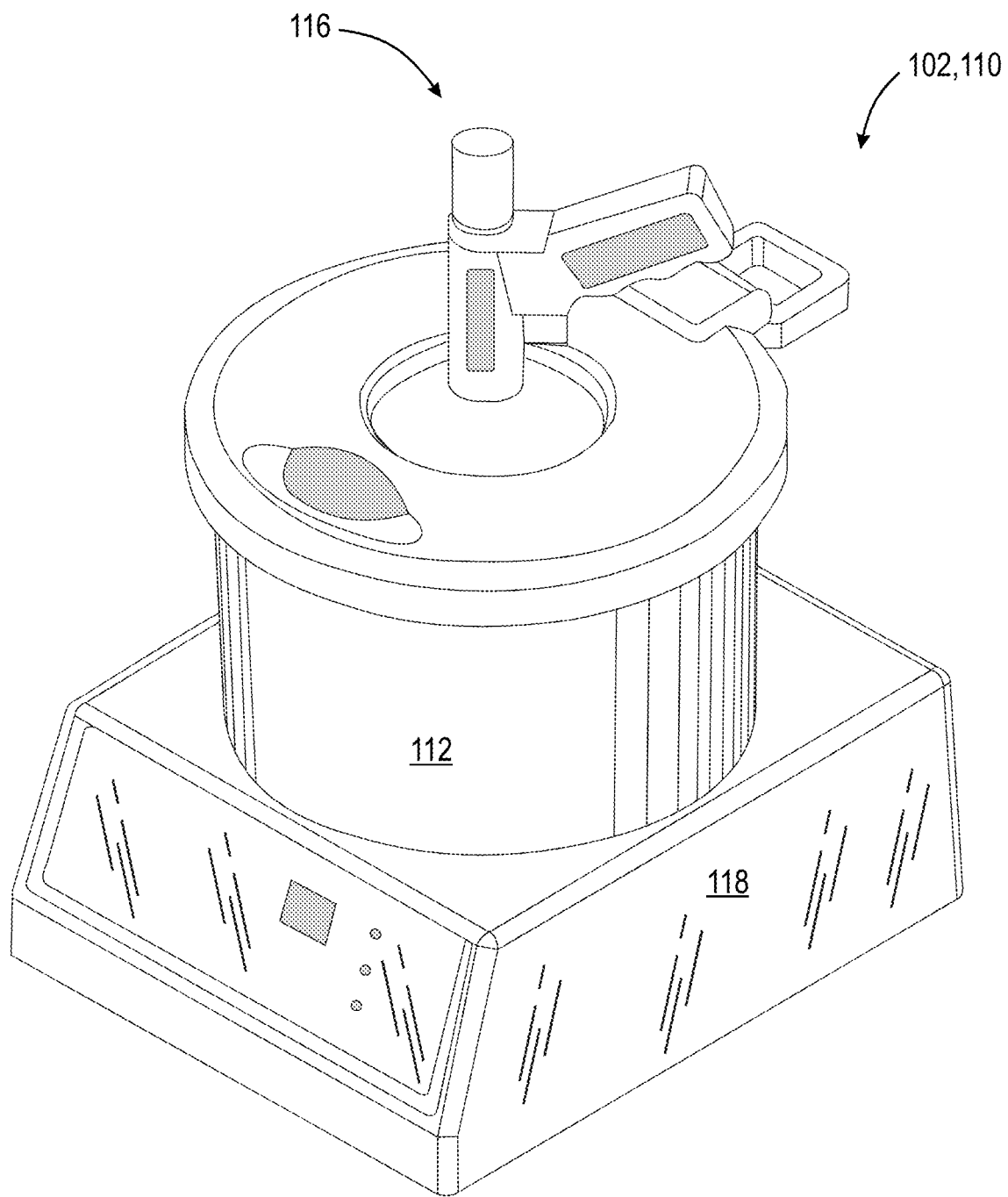
FIG. 3 is a schematic illustration of an irrigation system according to the present disclosure.

As will be disclosed herein in detail, should a user U determine that the patient P requires a cleaning operation to remove excess cerumen build-up in the patient's ear canal EC, and receives a granted permission request 156 (discussed below) to perform the cleaning operation, the user U can use at least one of a plurality of cleaning means 102 to remove the cerumen. For example, as shown in FIG. 2A, user U could utilize curette 106 or other cleaning means to scrape or otherwise manually remove the cerumen and discard it. In the alternative to, or in addition to, using curette 106, user U can utilize an automatic cleaning means, e.g., suction or irrigation. As shown in FIG. 2B, suction system 108 can include a pump or motor configured to generate a low pressure volume of air as well as a suction probe (not shown) attached to the low pressure volume via suction tubing. When the probe is inserted into the patient's ear canal EC the low pressure will draw in air and excess cerumen from the patient's ear.

Figure 4:
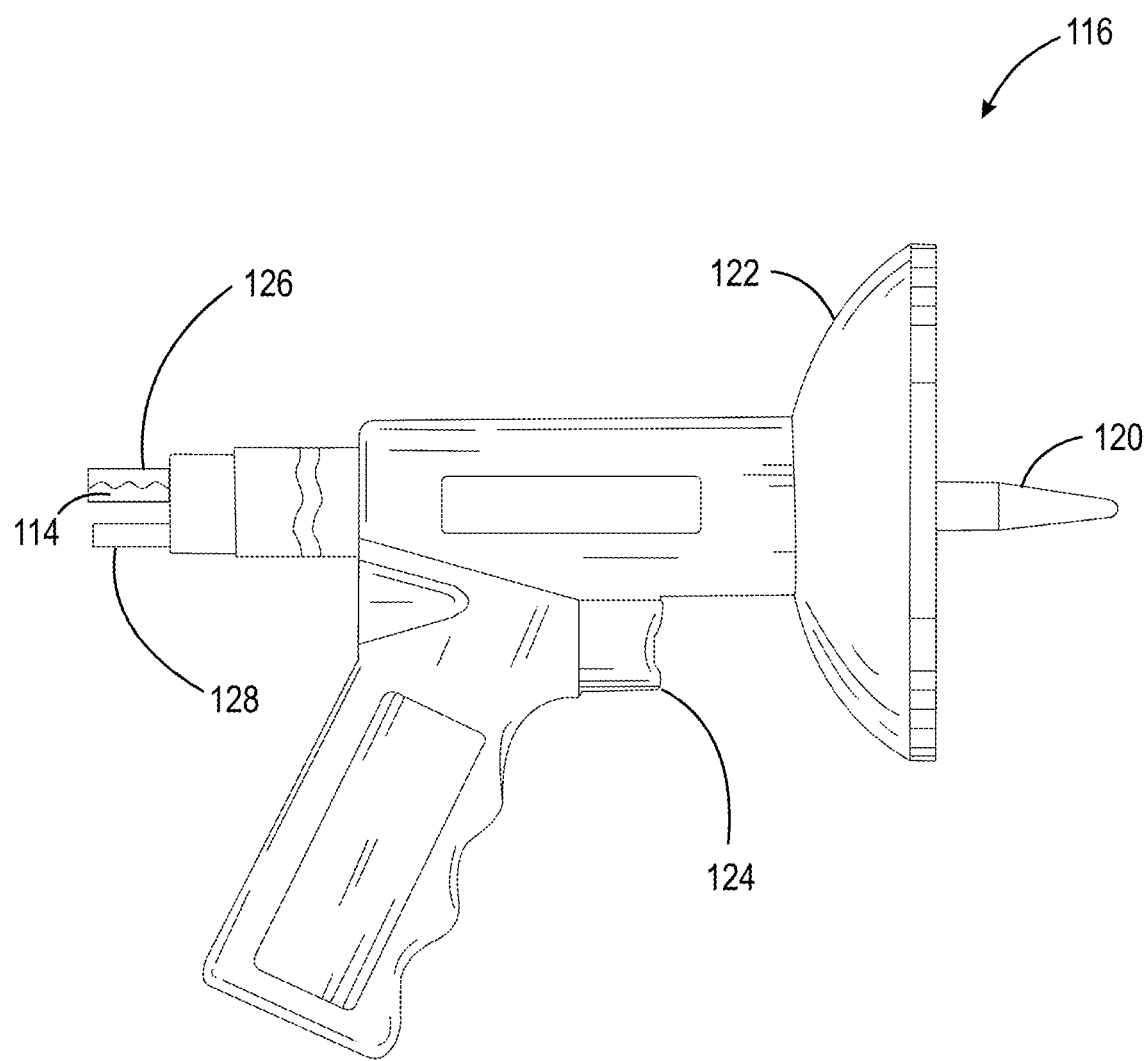
FIG. 4 is a schematic illustration of a portable applicator according to the present disclosure.

Irrigation system 110 can include simple mechanisms such as a hand syringe or spray bottle (not shown) or may be a more robust system as will be described below. For example, as illustrated in FIGS. 2C-4, irrigation system 110 can include a reservoir 112 to hold liquid 114, a portable applicator 116, and a control unit 118. Reservoir 112 is intended to be external or separate from control unit 118 and may be made of a material that is transparent, e.g., transparent acrylonitrile butadiene styrene (ABS) or transparent acrylic. Although not illustrated it should be appreciated that reservoir 112 can include an immersible heater that can be controlled by control unit 118 to preheat liquid 114 prior to a cleaning operation to the patient's ear canal EC to bring liquid 114 up to, e.g., body temperature. The external nature of reservoir 112 allows for ease of adding liquid to the reservoir 112. As shown in FIG. 4, portable applicator 116 includes a nozzle 120, transparent shield 122, trigger 124, fluid line 126, and control line 128. When a user U performs a cleaning operation using irrigation system 100, the user U can depress trigger 124 which sends a control signal through control line 128 to control unit 118 to pump fluid liquid 114 through fluid line 126 and out of nozzle 120. It should be appreciated that nozzle 120 can be configured to provide various flow patterns to fluid 114 and can come in a variety of shapes and sizes to fit within the patient's ear canal EC. Transparent shield 122 is intended to be made of a transparent glass or plastic material and has a concave-convex disc shape. While operating the portable applicator 116, user U can utilize the transparent shield 122 to see into the patient's ear canal and/or visually aid the user U in inserting nozzle 120 into the patient's ear E through visual magnification. Although not illustrated, transparent shield 122 may further include one or more focused light sources, e.g., light-emitting diodes (LEDs), to illuminate the patient's ear canal EC. Transparent shield 122 may also serve to contain the flow of liquid 114 and prevent back splash of liquid 114 and/or the cerumen-liquid combination exiting the patient's ear canal EC. Furthermore, although not illustrated, transparent shield 122, nozzle 120, or other portion of portable applicator 116 may include a camera to enable real-time video viewing of the patient's ear canal before, during, or after the cleaning operation is performed.

Although not illustrated in detail, control unit 118 can include a controller for regulating flow rate of liquid 114 from reservoir 112 to portable applicator 116, as well as regulating the current or voltage supplied to the heating element (not shown) within the reservoir to bring the liquid 114 to, e.g., body temperature. It should be appreciated that the controller can include a processor and memory configured to execute and store, respectively, a set of non-transitory computer-readable instructions to perform these functions as well as any other functions of control unit 118 mentioned herein. Systems for cleaning a patient's ear and methods of utilizing a portable applicator and irrigation system are discussed in additional detail in U.S. Pat. No. 9,993,591, titled "EAR CLEANING DEVICE," the entirety of which is herein incorporated by reference.

As will be described below, a user U may utilize peripheral device 104 to interact or otherwise engage with application 152, to request permission to perform the cleaning operations using the various cleaning means 102 described above. Peripheral device 104 includes body 130. Body 130 includes display 132, camera 134, and circuitry 136. In one example, display 132 is a Liquid-Crystal Display (LCD) and may also include touch-screen functionality, e.g., is capable of utilizing resistive or capacitive sensing to determine contact with, and position of, a user's finger against the screen surface. It should also be appreciated that display 132 can be selected from at least one of: a Light-Emitting Diode (LED) screen, an Organic Light-Emitting Diode (OLED) screen, a plasma screen, or any other display technology capable of presenting pictures or video to a viewer or user. As will be discussed below, the touchscreen capabilities of display 132 may be used to obtain or receive user input, i.e., user input 138, from user U. Camera 134 is intended to be a front-facing camera (shown in FIG. 5A) or rear-facing camera device (not shown) capable of capturing images of the environment surrounding user U and/or medical information related to the patient P, i.e., patient medical information 170 (discussed below).

Figure 5B:
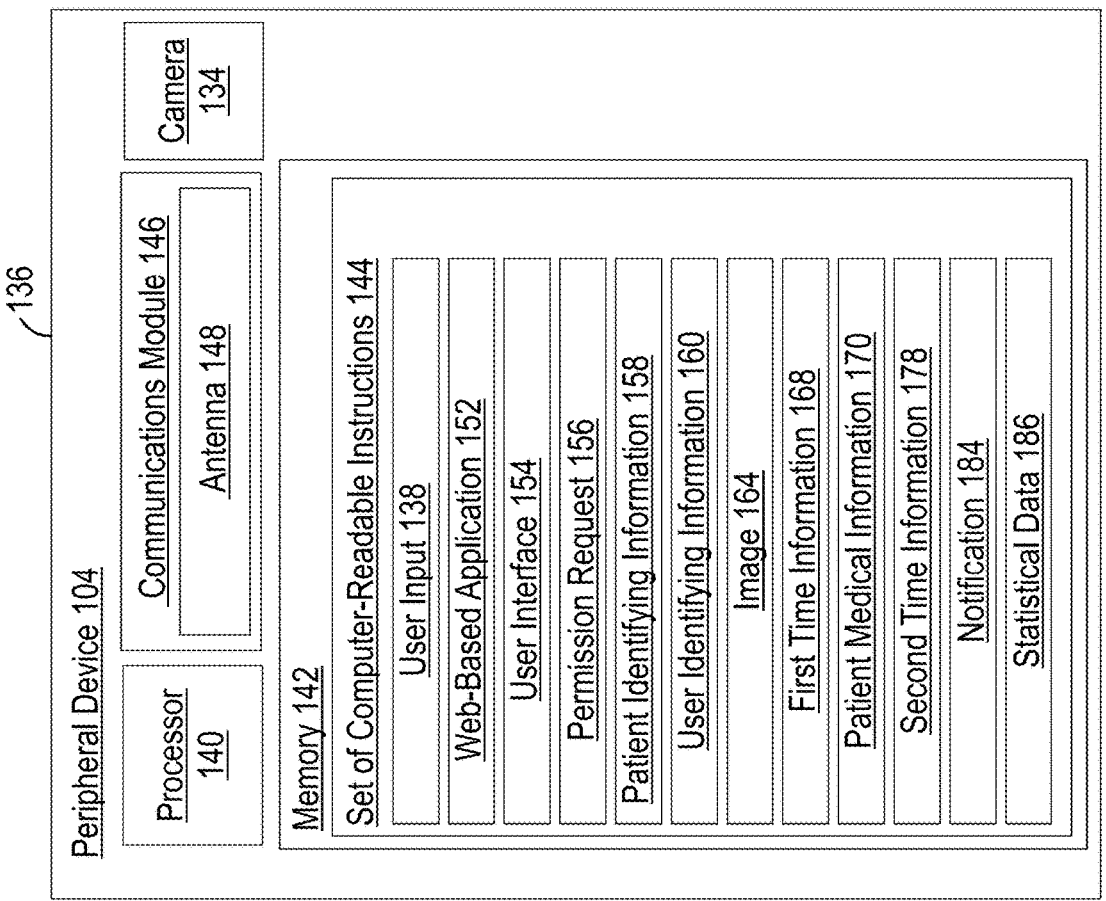
FIG. 5B is a schematic representation of the circuitry of a peripheral device according to the present disclosure.
Figure 5A:
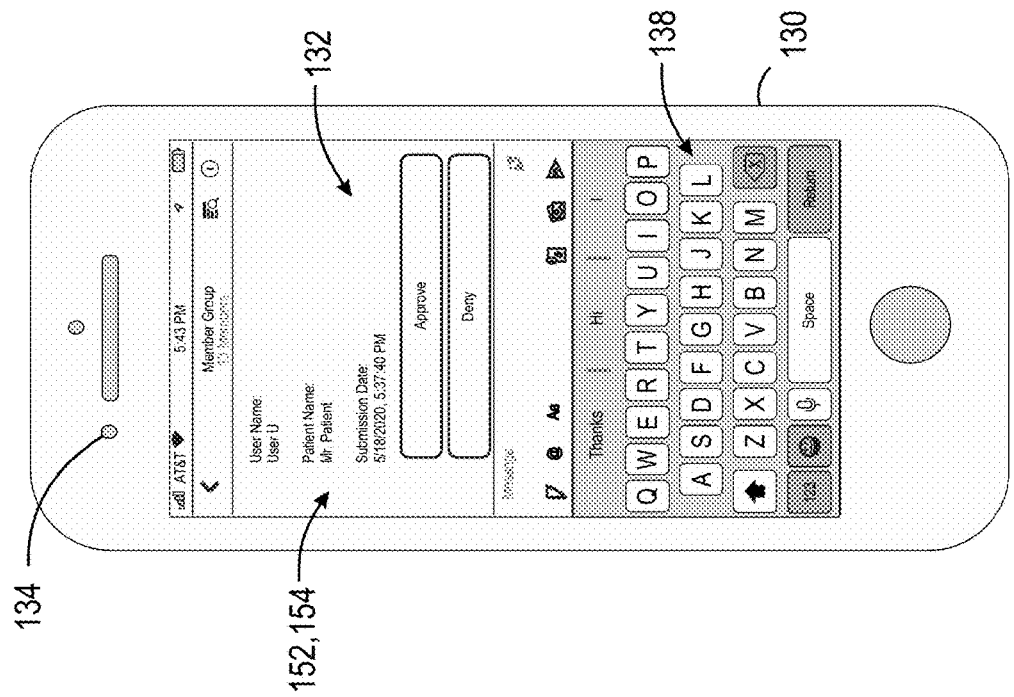
FIG. 5A is a schematic illustration of a peripheral device according to the present disclosure.

As illustrated schematically in FIG. 5B, circuitry 136 includes processor 140 and memory 142 configured to execute and store, respectively a set of non-transitory computer-readable instructions 144 to perform the functions of circuitry 136 and peripheral device 104 as described herein. Furthermore, as illustrated, circuitry 136 can also include a communications module 146 configured to establish a wired or wireless data connection with, e.g., the internet (not shown). To aid in establishing a wireless data connection, communications module 146 can include a wireless antenna, i.e., antenna 148, to send and receive wireless data. Additionally, and to these ends, circuitry 136 is intended to be a circuit, plurality of circuits, or plurality of electronic components that electrically connect display 132, camera 134, processor 140, memory 142, communications module 146, and antenna 148.

Figure 6:
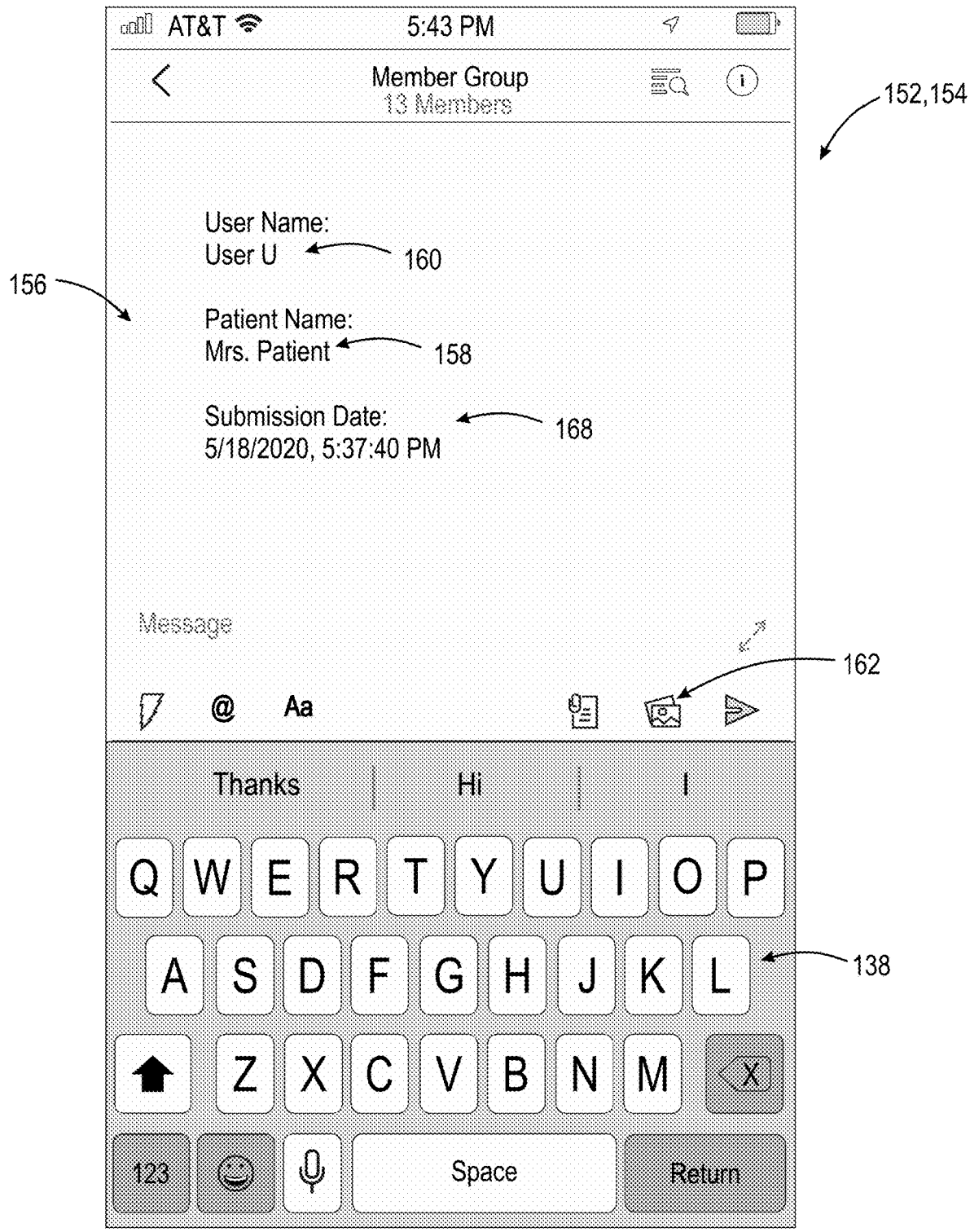
FIG. 6 is a schematic illustration of an application and user interface accordingly to the present disclosure.
Figure 7:
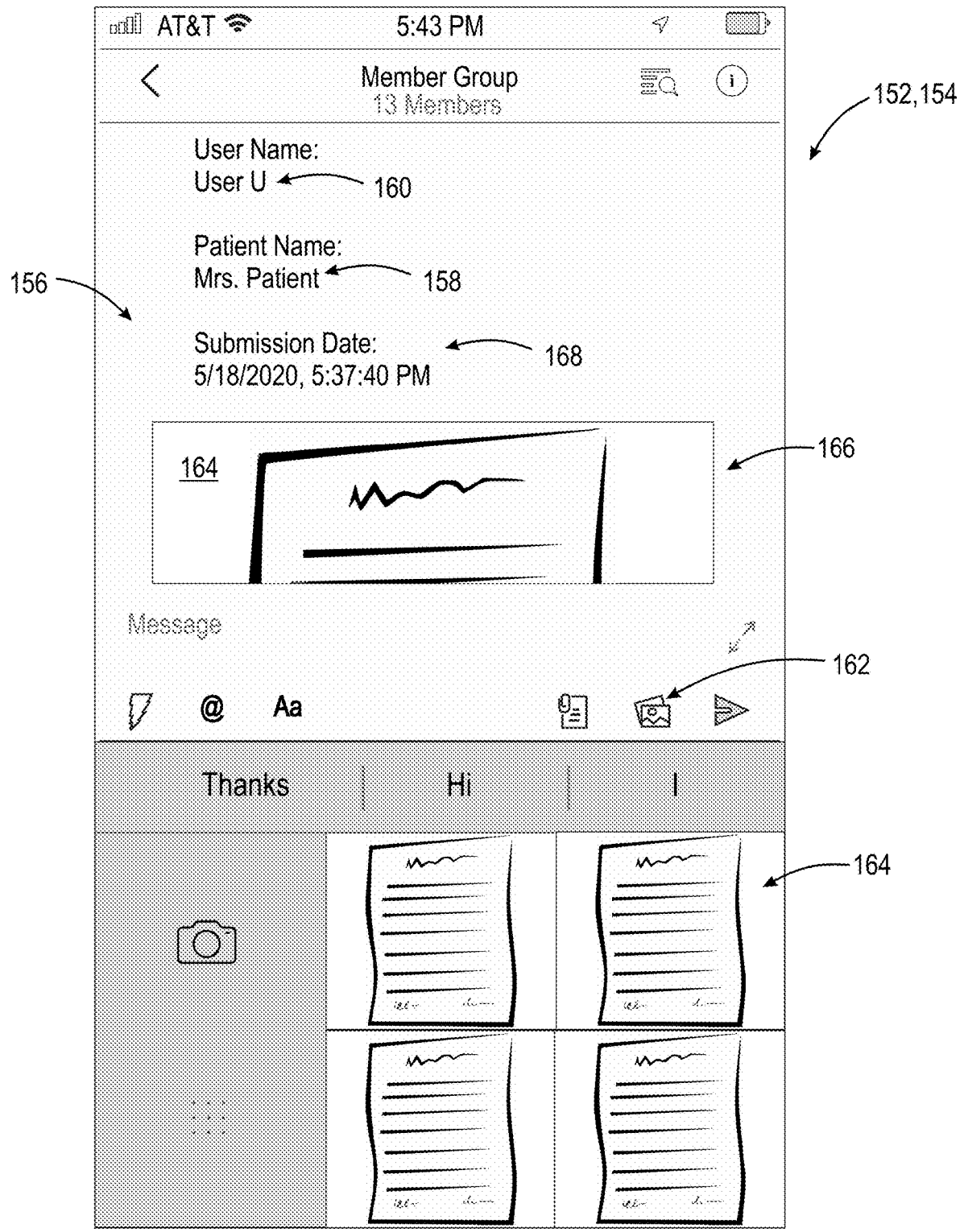
FIG. 7 is a schematic illustration of an application and user interface accordingly to the present disclosure.

The present application further includes a computer program product configured to allow a user to request permission from a licensed medical professional 150 (e.g., an Ear, Nose & Throat (ENT) Doctor) (shown in FIG. 10) through telemedicine techniques to grant the user U permission to perform a cleaning operation of a patient's ear canal EC using at least one of the cleaning means 102 described above. In one example, as shown in FIGS. 6-10, the computer program product can take the form of application 152. Application 152 is intended to be a web or network-based application, e.g., an application stored and executed on a remote server over the internet; however, it should be appreciated that application 152 can also be a native application, e.g., an application that is stored and executed on local memory of a device and does not require a connection to the internet to function. Thus, it should be appreciated that the instructions and functionality related to the execution and use of application 152 may be stored and executed on peripheral device 104, i.e., using processor 140 and memory 142; or can be stored and executed using a remote server over the internet. Application 152 includes a user interface 154 having several pages, or portions of a single page, that receive and/or display various pieces of information useful to the user U and/or the licensed medical professional 150 (shown in FIG. 10) in requesting permission to perform a cleaning operation and/or granting or denying permission requests 156. In one example, application 152 is a private group chat and/or communications application, e.g., can be a business communications platform such as Slack®, Flock, or Microsoft Teams®. As will be discussed below, the user interface 154 can have different configurations depending on whether the user U is preparing and sending a permission request 156 or whether the licensed medical professional 150 is receiving and/or evaluating the permission request 156. For example, as illustrated in FIGS. 6 and 7, when preparing a permission request 156, user interface 154 can include a portion for inputting and displaying patient identifying information 158 (e.g., the patient's name, gender, age/date of birth, etc.), a portion for displaying user identifying information 160 (e.g., the user U's name), a photograph gallery access portion 162 for selecting an image 164 (shown in FIG. 7 and discussed below) captured by camera 134, a portion for displaying first time information 168 related to the submission of the permission request 156, and a portion to receive any of this information from the user U, e.g., user input 138. It should be appreciated that application 152 may automatically identify and auto-fill user identifying information 160 based on detecting the identity of the device, an internet protocol address, device address, or account information entered by user U. Additionally, once the user U and/or patient P has input the relevant information into the request page of user interface 154, e.g., patient identifying information 158, user U and/or patient P can select a captured image, e.g., image 164 from the image gallery, (shown in FIG. 7) and once selected the request page of user interface 154 can include a portion for displaying the selected image, i.e., image display portion 166 (shown in FIG. 7). Additionally, and although not illustrated, in some examples, user U, patient P, or an algorithm may preemptively select a licensed medical professional 150. In these examples, permission request 156 may also contain a portion for displaying information related to the identity of the selected licensed medical professional 150 (e.g., the medical professional's name).

Image 164 is intended to be a photograph or other saved image which can contain patient medical information 170. In one example, patient medical information 170 may be gathered by user U prior to submission of permission request 156 to a licensed medical professional 150, where the patient medical information 170 can be received in the form of a paper questionnaire or waiver. The questionnaire or waiver can include questions and blank input fields for the patient P to input patient medical information 170 relating to: previous trauma or pain in their ear canal; whether the patient P has had a history of perforations (holes) in their eardrum within a predetermined period of time (e.g., five years); whether the patient P has experienced any ear pain; whether the patient P has experienced any ear-specific surgeries; whether the patient P has had a history of frequent ear infections; whether the patient P has had one or more previous ear cleaning operations and how often they have conducted such cleanings and what method or cleaning means 102 were used; and a section to write-in additional potential issues or complications that may be relevant to an ear cleaning procedure. The patient medical information 170 can also be provided in the form of a paper waiver having any combination of the foregoing information included where the patient P is prompted to sign their name affirming the accuracy of the answers provided. As will be discussed below, once user U has identified that the patient P requires a cleaning operation of their ear canal EC, the user U can instruct patient P to fill out a similar questionnaire or waiver as outlined herein, the user U can utilize peripheral device 104 to obtain an image 164 of the patient's medical information 170, e.g., by taking a photograph of the completed questionnaire or waiver with camera 134, and adding it to the permission request 156 so that it may be taken into account by the licensed medical professional 150 when evaluating the permission request 156. Although capturing an image, i.e., image 164, of a filled out questionnaire and uploading or otherwise adding it to the request is one method of obtaining patient medical information 170, it should be appreciated that other methods of obtaining and sending this information via application 152 are possible. For example, user U can manually enter the answers the patient P has provided via user input portion 138, i.e., by typing it out within the user interface 154. Additionally, the user U may record an audio file or sound file which includes the patient's answers to the questions provided in the waiver or questionnaire which can be attached to the request 156 in a similar fashion as image 164 described above.

Figure 8:
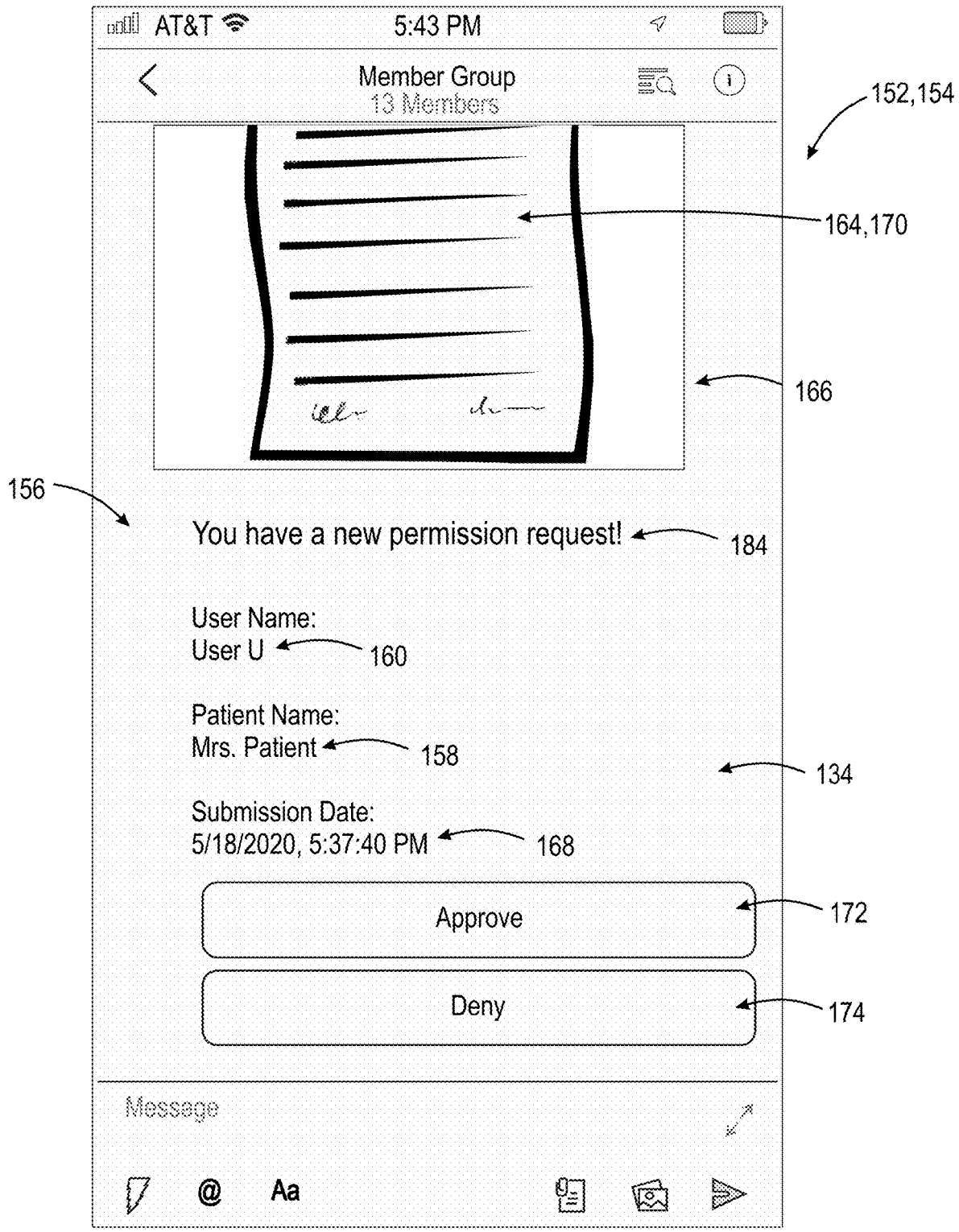
FIG. 8 is a schematic illustration of an application and user interface accordingly to the present disclosure.
Figure 9:
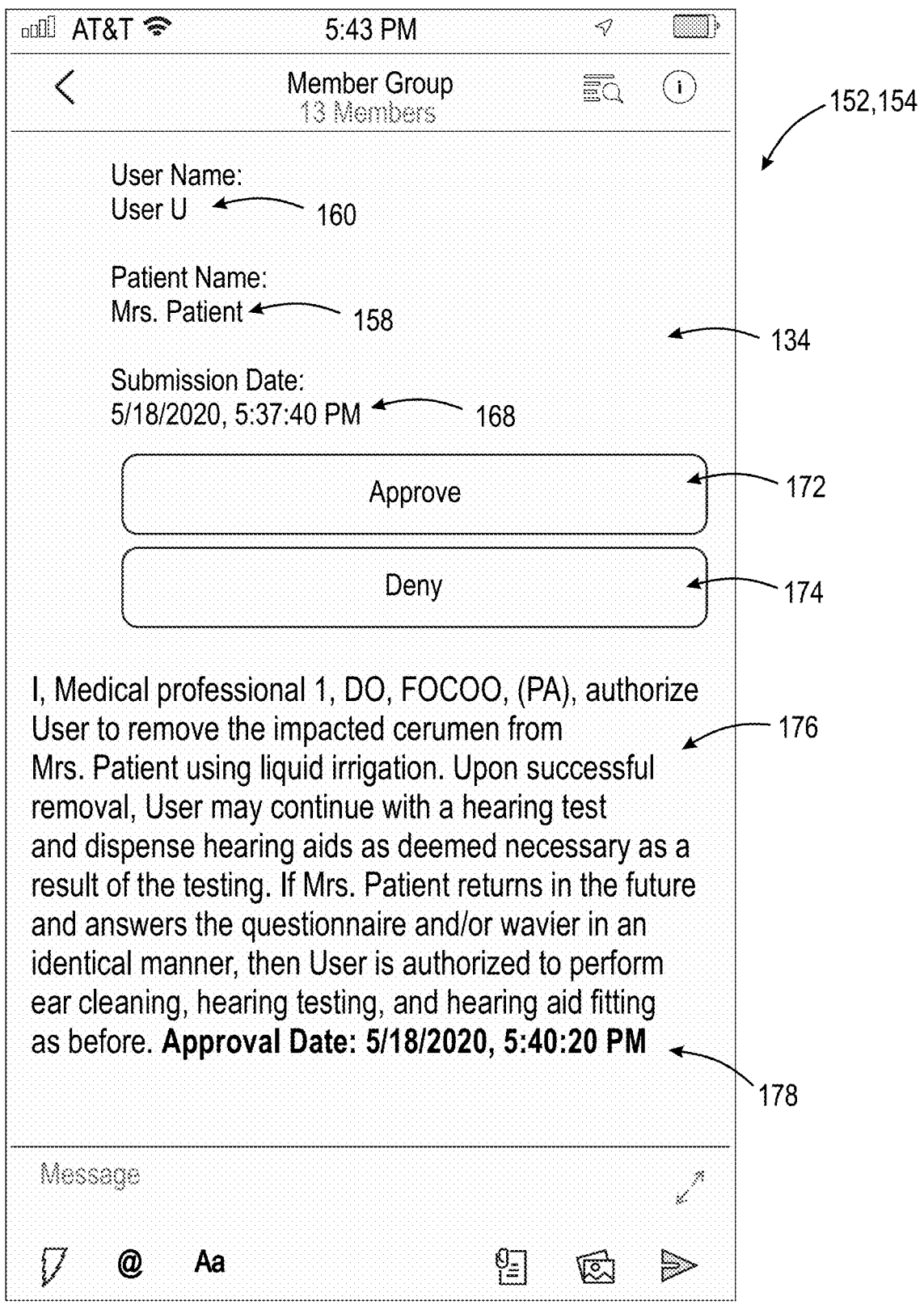
FIG. 9 is a schematic illustration of an application and user interface accordingly to the present disclosure.

As illustrated in FIGS. 8 and 9, when receiving and/or evaluating the permission request 156, user interface 154 includes the portion for displaying patient identifying information 158, the portion for displaying user identifying information 160, image display portion 166 (shown in FIG. 8), and the portion for displaying first time information 168 related to the submission of the permission request 156. Additionally, when receiving and/or evaluating permission request 156, user interface 154 may further include at least one portion dedicated to granting or approving a permission request 156, i.e., approve input portion 172 and at least one dedicated portion for denying permission requests 156, i.e., deny input portion 174.

Additionally, as illustrated in FIG. 9, when receiving and/or evaluating a permission request 156, user interface 154 can further include a long-form written authorization portion 176, which recites in clear and concise terms, the permission that is being granted by an approved permission request 156. For example, as illustrated, the written authorization portion 176, can include a statement from the identified medical professional, that they authorize the use of a particular form of cleaning means 102 and that the user U can continue with a hearing test. The written authorization portion 176 may also include a statement from the selected medical professional that if the patient P should return, and provide similar medical status information, e.g., fills out the questionnaire or waiver discussed above with similar answers, then the user U is authorized to perform a similar cleaning operation using the previously authorized cleaning means 102. Thus, it should be appreciated that, should the medical professional 150 grant the long-form written authorization portion 176, the granted permission request 156 can be a perpetual, e.g., continue until the patient P's medical information or situation changes. However, it should be understood that depending on the jurisdiction, municipality, state, or country within which user U is performing the cleaning operation and/or requesting permission, or depending on the jurisdiction, municipality, state, or country within which the licensed medical professional 150 resides when granting the permission request 156, a perpetual granting of the permission request may not be allowed and/or desired. Rather, in some jurisdictions, municipalities, states, or countries, the permission request may need to be renewed every visit, and/or after a certain number of visits as proscribed by the laws and guidelines of the subject jurisdictions. As illustrated, written authorization portion 176 can also include second time information 178 related to the current time and/or to the time a permission request 156 is approved or denied by the licensed medical professional 150. For example, second time information 178 may constantly update to the most current time while the licensed medical professional 150 is evaluating the permission request 156. However, once the licensed medical professional 150 grants or denies the permission request 156, e.g., by selecting the approve input portion 172 or the deny input portion 174, second time information 178 becomes fixed to the time of the submission. Additionally, should the licensed medical professional 150 select to deny the permission request 156, user interface 154 may also include a portion that allows the licensed medical professional 150 to provide a documented explanation for the reason for denial.

Figure 10:
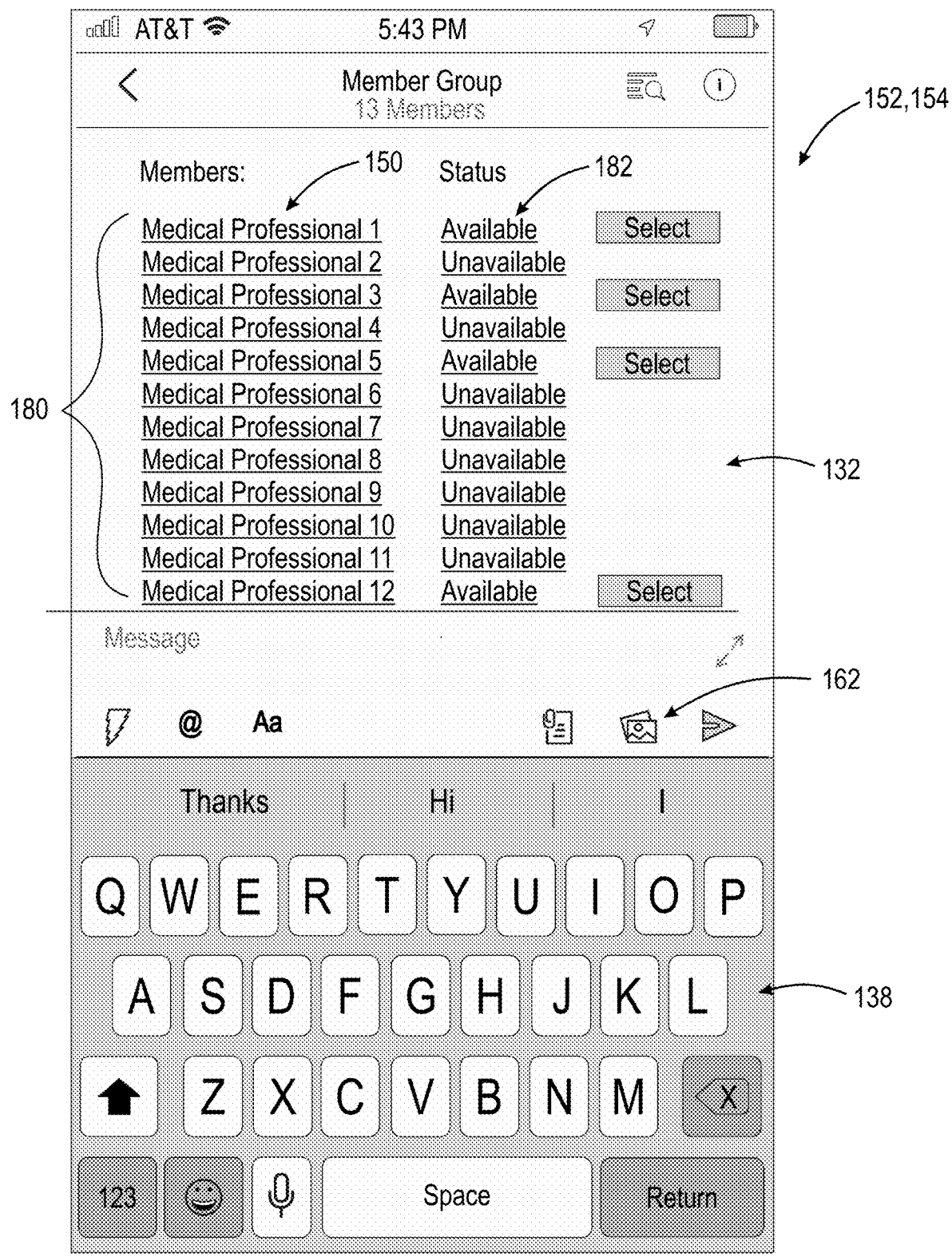
FIG. 10 is a schematic illustration of an application and user interface accordingly to the present disclosure.

In one example, at the time permission request 156 is submitted, the permission request 156 may be open-ended, e.g., may not be associated with a particular licensed medical professional 150 and can be accessible to all available licensed medical professionals 150 of a plurality of licensed medical professionals 180 (shown in FIG. 10). Each licensed medical professional 150 of plurality of licensed medical professionals 180 may receive a notification (e.g., notification 184 discussed below) that a new permission request has been submitted and may choose to evaluate the permission request 156 on a first come, first served basis. Alternatively, should a particular patient P have a prior relationship with one of the licensed medical professionals 150 of the plurality of licensed medical professionals 180, application 152 may automatically selected that particular licensed medical professional 150 and only provide the permission request 156 to that licensed medical professional 150. Similarly, the application 152 may only send a notification to the particular licensed medical professional 150.

Furthermore, user U and/or patient P may select a licensed medical professional 150 from the plurality of licensed medical professionals 180 from another section of the user interface 154 as illustrated in FIG. 10. As shown, each licensed medical professional 150 of plurality of licensed medical professionals 180 can be displayed along with a status indicator 182 to inform user U or patient P whether each particular licensed medical professional 150 is available to receive a new permission request. Thus, the user U or patient P can select one of the available licensed medical professionals 150 of the plurality of licensed medical professionals 180 based on their status indicator 182. It should be appreciated that although status indicator 182 is illustrated as a text-based identifier, status indicator 182 can be a visual identifier, e.g., green for available and red for unavailable. Additionally, and in the alternative to the foregoing, application 152 may utilize one or more algorithms to automatically select or suggest a licensed medical professional 150 from the plurality of license medical professionals 180 based on statistical data obtained by application 150, e.g., statistical data 186 (discussed below). Application 152 may also utilize one or more machine learning or deep learning algorithms to automatically select or suggest a licensed medical professional. The machine learning algorithm or deep learning algorithms can be supervised or unsupervised and can receive at least a portion of statistical data 186 (discussed below) as an input for training and/or implementation purposes. Specifically, the algorithm or algorithms discussed herein may utilize statistical data 186 (discussed below) to automatically selected or suggest a licensed medical professional, where the automatic selection or suggestion is based on one or more data selected from: licensure location of the medical professional 150, current availability (e.g., based on status indicator 182), average response time of the medical professional 150, average response accuracy of the medical professional 150, based on revenue balancing (e.g., based on cost of utilizing each available medical professional 150) or any other statistically relevant data to selecting a licensed medical professional 150.

Furthermore, plurality of licensed medical professionals 180 may be displayed or grouped based on a plurality of factors, including state licensure and other statistical data, e.g., statistical data 186 (discussed below). In one example, should the user U and/or patient P be located in New York, the plurality of licensed medical professionals 180 displayed to the user for selection or utilized by the algorithms discussed above for automatic selection and/or suggestion, may consist of only licensed medical professionals 150 that are licensed to practice medicine in the state of New York.

Additionally, and although not illustrated, it should be appreciated that user interface 154 may include a plurality of response options, e.g., where the available licensed medical professionals 150 can advertise that they will provide a response within, e.g., 5 minutes or 10 minutes. This information can be displayed proximate the licensed medical professional 150 and may act as an alternative to the status indicators 182 discussed herein. In this way, user U and/or patient P can select the licensed medical professional 150 from the plurality of licensed medical professionals 180 based on their advertised response time. Additionally, although not illustrated, it should be appreciated that after a given interaction with a licensed medical professional 150, user U and/or patient P may input, using user interface 154 a rating of their experience with the particular licensed medical professional 150. For example, the user U and/or patient P can provide a star rating or numerical rating out of a possible five stars or numerical rating scale to indicate their experience with the particular licensed medical professional 150.

The following example implementation of the methods disclosed herein should be read in view of FIGS. 1-10. An example implementation of telemedicine using the foregoing methods and systems begins with a patient P visiting a hearing aid dispenser where user U (e.g., a HIS described above) observes excess cerumen build-up in the patient's ear canal EC which must be removed prior to performing a hearing test. The user U may prompt the patient P to fill out a questionnaire or waiver form which includes patient medical information 170 related to prior ear related pain, trauma, or previous cleaning operations performed on the patient P. Once the patient P has filled out the questionnaire or waver, user U can obtain, using for example camera 134 of peripheral device 104, an image 164 of the filled out questionnaire or waiver and save it to memory 142 of peripheral device 104. The user U can then access application 152 and input, using for example user input portion 138, the patient's identifying information 158, and after selecting the photograph gallery access portion 162 can select the image 164 of the filled out questionnaire or waiver to include in the permission request 156. The user U may upload or submit the permission request 156 to a pool of licensed medical professionals 150 that have previously indicated they would participate in the program, i.e., plurality of licensed medical professionals 180. Each licensed medical professional 150 that is logged in or otherwise participating in the execution of the application 152, can receive a notification 184 that a new permission request 156 is available for their review and/or evaluation. One of the available licensed medical professionals 150 of the plurality of licensed medical professionals 180 can elect to evaluate the permission request 156, which excludes or locks out the other available licensed medical professionals 180 from accessing and evaluating the request 156. Alternatively, user U and/or patient P may select an available licensed medical professional 150 from the plurality of licensed medical professionals 180 based on a status indicator 182 and/or a previous relationship with the particular licensed medical professional. For example, the user U may simply want a quick resolution and can opt to select any available licensed medical professional 150, i.e., any licensed medical professional 150 of the plurality of licensed medical professionals 180 that are associated with an available status indicator 182. Once selected, the licensed medical professional 150 may then evaluate the permission request 156 using all of the information provided by user U as well as the patient medical information 170 contained in the image 164 of the questionnaire or waiver filled out by the patient P. Should the licensed medical professional 150 select to approve or deny the permission request 156, e.g., by selecting the approve input portion 172 or the deny input portion 174 of the user interface 154, the approved or denied request 156 will be sent back to user U via application 152. User U may choose to take a screen shot, i.e., capture an image of the current state of user interface 154 to capture the result of the request for their records. In the event that the selected licensed medical professional 150 approves the permission request 156, the user U may proceed with a cleaning operation of the patient's ear canal EC using the cleaning means 102 authorized by the request 156.

In some examples, user U may submit permission request 156 without checking, examining, or otherwise determining whether the patient P requires a cleaning operation of their ear canal EC. For example, user U may initiate or submit a permission request 156 upon patient P's entry into user U's building, office, or private patient examination room without first checking or determining whether the patient P has an excess of cerumen in one or more of their ear canals. Rather, this preemptive request of permission may be made before user U determines the cleaning operation is necessary and thus the time necessary for the licensed medical professional 150 to evaluate and grant the permission request occurs simultaneously with the patient's normal wait time, which lessens the total time of the patient P's visit improving the patient P's experience.

In evaluating the permission request 156, it should be appreciated that the licensed medical professional 150 may opt to communicate with user U and/or patient P to obtain more information. For example, the licensed medical professional 150 may, using peripheral device 104, initiate or receive a phone call from the licensed medical professional 150, initiate or receive a video call from the licensed medical professional 150, or send and/or receive at least one text message. Furthermore, the communication between user U and/or patient P with licensed medical professional 150 may be aided by a using a otoscope electrically connected to peripheral device 104 or portable applicator 116 to send real-time video data to licensed medical professional 150 showing the patient's ear canal EC, should the licensed medical professional 150 wish to see the patient's ear canal EC for themselves prior to approving or denying the permission request 156. It should be appreciated that any and all of the foregoing communication functionality may be provided or enabled through application 152.

The foregoing application 152 may operate to gather, obtain, and store statistical information or data, i.e., statistical data 186 which can be utilized by user U to evaluate the entire process set forth above and potentially provide information that could be useful in the day-to-day operations of the user U's business, i.e., be useful to a hearing aid dispenser. For example, statistical data 186 can include: the total or average number of patient's or patient encounters over a given time period, e.g., one day, one week, or one year, etc.; the total or average number of ear cleaning operations performed; the total or average number of approved permission requests 156; the total or average number of denied permission requests 156; a correlated list of reasons for denials; the total number of sales of hearing aids; of the patients that have had their ear's cleaned, how many purchased a hearing aid; the total or average amount of time it takes for a licensed medical professional 150 to approve or deny a permission request 156; the total or average time it takes to perform a cleaning operation; the total number of cleaning operations specific to each cleaning means 102; how often a particular licensed medical professional 150 requests additional communication with the user U or patient P; performance evaluation data on particular licensed medical professionals 150 based on ratings submitted by the user U or patient P; and total or average amount of money billed to insurance companies related to time spent using application 152.

The foregoing statistical data 186 can be useful to at least hearing aid dispenser businesses in that the number of patients cleaned, the billing revenue generated for the service of cleaning (which can either be collected at the time the service is rendered, or billed to medical insurance) and the number of hearing aids sold after those cleanings provides data related to the return-on-investment of purchasing the apparatuses required to perform certain cleaning operations, e.g., justify the purchase of an irrigation system 110. Based on the total number of cleanings and how long each cleaning takes the business could determine return-on-investment per hour. Knowing how often patient's return to have their ear's cleaned can aid in predicting future revenue. Capturing the time it takes a licensed medical professional 150 to respond and provide an approval or denial helps to evaluate which licensed medical professionals 150 are routinely attentive. This is also very important statistic to the user U as the patient P is sitting and waiting until the approval/denial comes through and can lead to better patient experiences. Being able to upload the statistical data 186 to third parties is also beneficial as the statistical information could be provided directly to a billing system for health insurance reimbursement purposes and can be utilized to help the user U secure insurance contracts. It can also allow the user U to keep statistics on reimbursement amounts and by which insurance companies.

Furthermore, statistical data 186 can be utilized by the present system to display historical data related to the patient P, the user U, and/or the selected licensed medical professional 150. For example, the page or portion of the page of user interface 154 utilized by user U to submit the permission request 156 can include a portion that displays historical data of the patient P, e.g., the number of past cleanings, average time between cleanings, past trauma to the ear, or any other statistically relevant data related to approving or denying the permission request 156. Similarly, on the page or portion of the page of user interface 154 utilized by the licensed medical professional 150 to evaluate the permission request 156, there may be a portion or portions that display historical data of the patient P (e.g., the data discussed above) and/or data related the user U. For example, the display portion may include data on how many requests have been sent by user U, how many grants/denials have been provided to user U, average response time to all of user U's requests, or any other statistically relevant data related to approving or denying the permission request 156, or servicing user U.

Figure 11:
FIG. 11 is a flow chart illustrating the steps of a method according to the present disclosure.

FIG. 11 illustrates a flow chart showing the steps of an exemplary implementation of method 200 of the present disclosure. Method 200 can include, for example: determining whether an ear canal EC of the patient P requires a cleaning operation (step 202); determining whether the patient P is eligible for receiving a cleaning operation, where determining eligibility includes whether the patient P has experienced trauma or pain in their ear canal EC (step 204); obtaining an image 164 from at least one camera 134, the image 164 including patient medical information 170 related to the patient P (step 206); sending, via the application 152, the image 164 to the licensed medical professional 150 (step 208); sending, via application 152, a permission request 156 to a licensed medical professional 150, the permission request 156 corresponding with a request for permission to perform a cleaning operation of the patient's ear canal EC (step 210); determining, by the licensed medical professional 150, whether to grant or deny the permission request 156 to perform the cleaning operation of the ear canal EC of the patient P based at least in part on patient medical information 170 related to the patient P (step 212); receiving, via the application 152, a granted permission request 156 from the licensed medical professional 150 (step 214); and performing a cleaning operation of the ear canal EC of the patient P (step 216).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The above-described examples of the described subject matter can be implemented in any of numerous ways. For example, some aspects may be implemented using hardware, software or a combination thereof. When any aspect is implemented at least in part in software, the software code can be executed on any suitable processor or collection of processors, whether provided in a single device or computer or distributed among multiple devices/computers.

The present disclosure may be implemented as a system, a method, and/or a computer program product at any possible technical detail level of integration. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some examples, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to examples of the disclosure. It will be understood that each block of the flowchart illustrations and/or block diagrams, and combinations of blocks in the flowchart illustrations and/or block diagrams, can be implemented by computer readable program instructions.

The computer readable program instructions may be provided to a processor of a, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other implementations are within the scope of the following claims and other claims to which the applicant may be entitled.

While various examples have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the examples described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific examples described herein. It is, therefore, to be understood that the foregoing examples are presented by way of example only and that, within the scope of the appended claims and equivalents thereto, examples may be practiced otherwise than as specifically described and claimed. Examples of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

What is claimed is:

1. A method for treating an ear canal of a patient via a cleaning operation, wherein the patient is suffering from obstructive or impacted cerumen, the method comprising:
   determining whether an ear canal of the patient requires a cleaning operation based on observed cerumen within the ear canal by:
      examining the ear canal of the patient via an otoscope; and
      detecting, via the examination, obstructive or impacted cerumen within the ear canal of the patient;
   if the patient requires the cleaning operation, sending, via an application, a permission request to a device corresponding to a licensed medical professional, the permission request corresponding with a request for permission to perform a cleaning operation of the patient's ear canal;
   receiving, via the application, a granted permission request from the device corresponding to the licensed medical professional in response to the sent permission request, wherein the granted permission request corresponds to an input from the licensed medical professional; and performing, if the granted permission is received via the application, the cleaning operation of the ear canal of the patient, wherein performing the cleaning operation of the patient's ear canal includes manually cleaning the patient's ear canal, cleaning the patient's ear canal using suction, and/or cleaning the patient's ear canal using an irrigation system.

2. The method of claim 1, wherein manually cleaning the patient's ear canal comprises using a curette, forceps, or tweezers.

3. The method of claim 1, wherein the irrigation system comprises:

a portable applicator arranged to engage with and perform a cleaning operation on the ear canal of the patient;

a liquid reservoir arranged to contain a fluid, the liquid reservoir comprising a heater for heating the fluid; and a control unit operatively arranged to control the heater of the liquid reservoir and operatively arranged to control a pump arranged between the liquid reservoir and the portable applicator such that the control unit can dynamically vary a flow rate of the fluid from the portable applicator.

4. The method of claim 1, further comprises:

determining whether the patient is eligible for receiving the cleaning operation, where determining eligibility includes whether the patient has experienced trauma, pain in their ear canal, or has previously had surgery related to their ear.

5. The method of claim 1, wherein the method further comprises:

obtaining an image from at least one camera, the image including medical information related to the patient; and sending, via the application, the image to the device corresponding to the licensed medical professional.

6. The method of claim 1, further comprising:

receiving, by the device corresponding to the licensed medical professional, the permission request sent via the application; and determining, by the licensed medical professional prior to providing the granted permission request, whether to grant or deny the permission request to perform the cleaning operation of the ear canal of the patient based at least in part on medical information related to the patient.

7. The method of claim 1, wherein the licensed medical professional is selected from a plurality of licensed medical professionals in communication with the application.

8. The method of claim 7, wherein the selection of the licensed medical professional from the plurality of licensed medical professionals is based on a status indicator provided by the application or an algorithm used by the application.

9. The method of claim 1, wherein the application is configured to obtain statistical data relating a total number granted permission requests, a total number of denied permission requests, or an average time duration for granting or denying the permission requests.

10. A computer program product for obtaining authorization to treat an ear canal of a patient via a cleaning operation, wherein the patient is suffering from obstructive or impacted cerumen, the computer program product including a set of non-transitory computer-readable instructions stored on a memory that when executed on a processor are configured to:

send a permission request to a device corresponding to a licensed medical professional, the permission request corresponding with a request for permission to perform the cleaning operation of the patient's ear canal, wherein the permission request is sent if the ear canal of the patient requires a cleaning operation based on observed cerumen within the ear canal by:

examining the ear canal of the patient via an otoscope; and detecting, via the examination, obstructive or impacted cerumen within the ear canal of the patient; and receive a granted permission request from the device corresponding to the licensed medical professional in response to the sent permission request, wherein the granted permission request corresponds to an input from the licensed medical professional;

wherein the granted permission request prompts an individual to perform, if the granted permission is received via the application, the cleaning operation of the patient's ear canal, wherein performing the cleaning operation of the patient's ear canal includes manually cleaning the patient's ear canal, cleaning the patient's ear canal using suction, and/or cleaning the patient's ear canal using an irrigation system.

11. The computer program product of claim 10, wherein manually cleaning the patient's ear canal comprises using a curette, forceps, or tweezers.

12. The computer program product of claim 10, wherein the irrigation system comprises:

a portable applicator arranged to engage with and perform a cleaning operation on the ear canal of the patient;

a liquid reservoir arranged to contain a fluid, the liquid reservoir comprising a heater for heating the fluid; and a control unit operatively arranged to control the heater of the liquid reservoir and operatively arranged to control a pump arranged between the liquid reservoir and the portable applicator such that the control unit can dynamically vary a flow rate of the fluid from the portable applicator.

13. The computer program product of claim 10 wherein the processor is further configured to:

obtain an image from at least one camera, the image including medical information related to the patient; and send the image to the device corresponding to the licensed medical professional.

14. The computer program product of claim 10, wherein the processor is further configured to:

send and receive patient medical data related to determining whether the patient is eligible for receiving the cleaning operation, including whether the patient has experienced trauma, pain in their ear canal, or has previously had surgery related to their ear.

15. The computer program product of claim 10, wherein the processor is further configured to display, via the application, prior to sending the permission request, a list representing a plurality of licensed medical professionals.

16. The computer program product of claim 15, wherein the processor is further configured to:

receive a user input selecting the licensed medical professional from the plurality of licensed medical professionals.

17. The computer program product of claim 15, wherein the selection of the licensed medical professional is selected based on a status indicator or based on an algorithm.

18. The computer program product of claim 10, wherein the processor is further configured to:
   obtain statistical data relating a total number granted permission requests, a total number of denied permission requests, or an average time duration for granting or denying the permission requests.

* * * * *